United States Patent
Pfeiffer et al.

(10) Patent No.: US 9,473,070 B2
(45) Date of Patent: Oct. 18, 2016

(54) APPARATUS FOR DETERMINING AND/OR MONITORING AT LEAST ONE PROCESS VARIABLE

(71) Applicant: Endress + Hauser GmbH + Co. KG, Maulburg (DE)

(72) Inventors: Helmut Pfeiffer, Steinen (DE); Benjamin Mack, Lorrach (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 172 days.

(21) Appl. No.: 14/364,098

(22) PCT Filed: Nov. 22, 2012

(86) PCT No.: PCT/EP2012/073377
§ 371 (c)(1),
(2) Date: Jun. 10, 2014

(87) PCT Pub. No.: WO2013/087392
PCT Pub. Date: Jun. 20, 2013

(65) Prior Publication Data
US 2014/0320224 A1    Oct. 30, 2014

(30) Foreign Application Priority Data
Dec. 12, 2011 (DE) .................. 10 2011 088 304

(51) Int. Cl.
*H01L 41/09* (2006.01)
*H01L 41/113* (2006.01)
(Continued)

(52) U.S. Cl.
CPC ............ *H03B 5/30* (2013.01); *G01F 23/2967* (2013.01); *G01N 9/002* (2013.01); *G01N 11/16* (2013.01)

(58) Field of Classification Search
USPC .................. 310/311, 322, 324, 328, 333, 336
See application file for complete search history.

(56) References Cited

U.S. PATENT DOCUMENTS 3,131,515 A * 5/1964 Mason .......................... 451/28
5,631,633 A * 5/1997 Dreyer et al. .............. 340/621
(Continued)

FOREIGN PATENT DOCUMENTS

DE       8601452.8 U1    6/1989
DE    102005053331 A1    5/2007
(Continued)

OTHER PUBLICATIONS

German Search Report, German PTO, Munich, Jul. 17, 2012.
(Continued)

*Primary Examiner* — Thomas Dougherty
(74) *Attorney, Agent, or Firm* — Bacon & Thomas, PLLC

(57) ABSTRACT

An apparatus for determining and/or monitoring at least one process variable of a medium, comprising: an oscillatable unit, which has a membrane and at least one oscillatable element, wherein the oscillatable element is secured to the membrane at least in a first securement region and in a second securement region. At least one driving/receiving unit, which excites the oscillatable unit to execute mechanical oscillations and which produces a received signal dependent on the oscillations of the oscillatable unit; and a control/evaluation unit, which evaluates the received signal with reference to the process variable. The apparatus is distinguished by features including that the driving/receiving unit is embodied in such a manner and arranged on a rear face of the membrane facing away from the oscillatable element that the oscillatable element executes torsional oscillations.

11 Claims, 3 Drawing Sheets

(51) Int. Cl.
  *H01L 41/053*  (2006.01)
  *H03B 5/30*  (2006.01)
  *G01N 9/00*  (2006.01)
  *G01N 11/16*  (2006.01)
  *G01F 23/296*  (2006.01)

(56) References Cited

U.S. PATENT DOCUMENTS

| | | | |
|---|---|---|---|
| 5,743,134 A * | 4/1998 | Dreyer | 73/290 V |
| 7,075,216 B1 * | 7/2006 | Vetelino | 310/338 |
| 7,893,603 B2 | 2/2011 | Lopatin | |
| 8,261,615 B2 * | 9/2012 | Lopatin et al. | 73/649 |
| 8,434,350 B2 * | 5/2013 | Urban et al. | 73/32 A |
| 2004/0093941 A1 * | 5/2004 | Lopatin | 73/290 V |
| 2008/0257036 A1 * | 10/2008 | Chaudoreille et al. | 73/32 A |
| 2010/0030486 A1 * | 2/2010 | Lopatin et al. | 702/24 |
| 2013/0091946 A1 * | 4/2013 | Knowles et al. | 73/290 V |
| 2013/0139576 A1 * | 6/2013 | Goodbread et al. | 73/64.53 |
| 2015/0075279 A1 * | 3/2015 | Donzier | 73/32 A |

FOREIGN PATENT DOCUMENTS

| | | |
|---|---|---|
| DE | 102006031188 A1 | 1/2008 |
| JP | 7008913 A | 1/1995 |
| WO | 2005085769 A2 | 9/2005 |

OTHER PUBLICATIONS

International Search Report, EPO, The Netherlands, May 29, 2013.
English translation of the International Preliminary Report, WIPO, Geneva, Nov. 22, 2012.

* cited by examiner

APPARATUS FOR DETERMINING AND/OR MONITORING AT LEAST ONE PROCESS VARIABLE

TECHNICAL FIELD

The present invention relates to an apparatus for determining and/or monitoring at least one process variable of a medium, and includes: an oscillatable unit, which has a membrane, or diaphragm, and at least one oscillatable element, wherein the oscillatable element is secured to the membrane at least in a first securement region and in a second securement region; at least one driving/receiving unit, which excites the oscillatable unit to execute mechanical oscillations and which produces a received signal dependent on the oscillations of the oscillatable unit; and a control/evaluation unit, which evaluates the received signal with reference to the process variable. The process variable is, for example, the fill level, the density and/or the viscosity of a medium. The medium can, in such case, be present in the form of a liquid or a gas. The oscillatable unit is, for example, a rod formed on a membrane or an oscillatory fork having two paddle shaped oscillatory elements secured to a membrane.

BACKGROUND DISCUSSION

Known from laid-open German Application [Offenlegungsschrift] DE102006031188 A1 is an apparatus for determining and/or monitoring a process variable. Secured on a membrane in this disclosure is an oscillatory element, which, due to the special way in which it is embodied, is excited to execute torsional oscillations. The membrane is, in such case, deflected in such a manner that it executes a transverse movement perpendicular to the membrane surface, i.e. it oscillates in the fundamental mode. The oscillatory element is embodied in such a manner and secured with two connection regions on the membrane that the two connecting regions in the case of this movement of the membrane experience differently directed force components and the oscillatory element executes a torsional movement.

Furthermore, vibronic measuring devices are known, which have a so-called oscillatory fork as the mechanically oscillatable unit. Oscillatory forks permit, on the one hand, fill level and density measurements, while, on the other hand, also enabling measurement of viscosity. The oscillatory fork is, most often, excited by means of a driving/receiving unit in the form of one or more piezoelectric elements to execute bending oscillations. In such case, the two paddles forming the oscillatory fork execute bending movements of opposite phase. For fill level measurement, the oscillation frequency is monitored. For viscosity measurement, most often, the amplitude of the oscillations is evaluated. Due to the added-mass effect because of dragged medium, application for higher viscosity media is, however, problematic.

SUMMARY OF THE INVENTION

An object of the invention is to provide an apparatus for determining and/or monitoring at least one process variable, which also measures reliably in applications involving high viscosity media.

The object is achieved by features including that the driving/receiving unit is embodied in such a manner and arranged on a rear face of the membrane facing away from the oscillatable element that the driving/receiving unit excites the membrane to execute oscillations in such a manner that a first section of the membrane, in which the first securement region is located, and a second section of the membrane, in which the second securement region is located, execute oscillations of opposite phase, and the oscillatable element executes torsional oscillations. The torsional oscillations are preferably oscillations in the torsion mode with the eigenfrequency of the at least one oscillatable element. In the torsional oscillations, for example, two points of the oscillatable element arranged mirror symmetrically relative to a longitudinal axis move in opposite directions. In contrast to this, in the case of bending oscillations, all points composing the oscillatable element move in the same direction.

Because of the particular embodiment and arrangement of the driving/receiving element, the oscillatable element is caused to oscillate torsionally. An advantage of torsional oscillations compared with bending oscillations is that, at most, a smaller effect as concerns dragged mass occurs, so that the apparatus is also applicable in media with high viscosity and the process variable is reliably determinable. The torsion mode is excited through the opposite phase oscillations of the two sections of the membrane, in which, in each case, a securement region of the oscillatable element is located.

The torsion mode is evaluatable, for example, with reference to fill level and density. For fill level measurement, as in the case of the exciting of a bending mode, the ex- or sub-ceeding of a limit frequency is evaluated. The limit frequency between covered state and free state just lies at another position than in the case of the exciting in a bending mode. Especially, the torsion mode is suited, however, for determining and/or monitoring the viscosity of the medium, with which the oscillatable unit is in contact. For viscosity measurement, the control/evaluation unit evaluates, for example, the amplitude and/or the frequency of the oscillations. Because of the small added-mass effect, the apparatus of the invention is especially suitable as a viscosimeter.

In an embodiment, the oscillatable element is at least sectionally paddle shaped or rod shaped. A rod shaped oscillatable element has, for example, a circular or oval base. In the case of a cylindrical oscillatable element, the dragged mass is especially small.

In an additional embodiment, the driving/receiving unit includes at least one piezoelectric drive element. For receiving the mechanical oscillations of the oscillatable unit and conversion into an electrical received signal, the driving/receiving unit can have at least one additional piezoelectric element. Alternatively, the drive element can, however, serve simultaneously also as receiver.

In an embodiment, the drive element is polarized perpendicularly to a plane, in which the membrane lies in a relaxed state. The drive element can, in such case, be polarized homogeneously in one direction, or be divided into two regions, which are polarized in opposite directions. In each case, these are axial polarizations.

Another embodiment provides that the driving/receiving unit has at least two symmetric regions electrically insulated from one another and is arranged in such a manner that the first region extends over the first section of the membrane, in which at least the first securement region of the oscillatable element is located and that the second region extends over the second section of the membrane, in which at least the second securement region of the oscillatable element is located. In an embodiment, the driving/receiving unit has only one drive element, which is divided into two symmetric regions. The subdividing is produced, for example, by the arranging of sending electrodes on the surface of the drive element. Each of the two regions serves for exciting one of the two sections of the membrane to execute oscillations. In an alternative form of embodiment, for exciting the two membrane sections to opposite phase oscillations, the two regions of the driving/receiving unit are implemented by two separately embodied drive elements. The two sections of the membrane, which are excited by the driving/receiving unit to execute mechanical oscillations of opposite phase, are symmetric to a central axis of the membrane. The two drive elements are, consequently, formed preferably essentially symmetrically to one another and arranged symmetrically to the central axis. Preferably, the two drive elements possess the shape of circular sections; this especially in the case of a circularly shaped membrane. The driving/receiving unit is in each case embodied in such a manner that the two regions of the piezoelectric drive element, respectively the two piezoelectric drive elements, execute thickness oscillations of opposite phase.

In an embodiment, a first oscillatable element and a second oscillatable element are secured to the membrane essentially symmetrically to a central axis of the membrane.

An embodiment associated therewith provides that the driving/receiving unit and the two oscillatable elements are arranged in such a manner relative to one another that the first region of the driving/receiving unit extends over the first section of the membrane, in which at least the first securement region of the first oscillatable element and the first securement region of the second oscillatable element are located, and that the second region of the driving/receiving unit extends over the second section of the membrane, in which at least the second securement region of the first oscillatable element and the second securement region of the second oscillatable element are located. Acting on the two oscillatable elements are, in each case, forces directed oppositely to one another. In this way, the oscillations are decoupled and no force, or, at most, a negligibly low force, acts on the mounting of the membrane. The central axis of the membrane, with respect to which the two oscillatable elements are symmetrically arranged, and the central axis, which lies between the two sections of the membrane oscillating with opposite phase and relative to which the two regions of the driving/receiving unit are symmetric, extend orthogonally to one another.

Another embodiment provides that the two regions of the driving/receiving unit have, in each case, a sending electrode and the control/evaluation unit supplies the sending electrodes, in each case, with an alternating voltage signal of equal frequency, wherein for the case, in which the two regions have the same polarization direction, the two alternating voltage signals have relative to one another a phase shift of 180° and for the case, in which the two regions have opposite directions of polarization, the two alternating voltage signals are of equal phase. Because of the polarization direction and the correspondingly selected type of supply with the exciter signal, the two regions execute thickness oscillations of opposite phase, which leads to an opposite phase deflection of the two membrane sections, where the two regions of the driving/receiving unit are arranged.

For supplying the piezoelectric drive element, respectively the piezoelectric drive elements, with an exciter signal, two sending electrodes are applied on that surface of the drive element, respectively the drive elements, which face(s) away from the membrane. In the case of a circularly shaped membrane, the drive element is likewise circular and the two sending electrodes have the shape of two circular segments spaced from one another. In the case of a two-part embodiment, two drive elements are provided in the form of circular segments with sending electrodes, which are likewise shaped as circular segments. For example, the sending electrodes are applied as metal coatings of the drive element, respectively the drive elements. Those surfaces of the drive element, respectively the drive elements, which contact the membrane, are preferably coated with a 2-dimensional electrode connected to ground potential. The terminology "2-dimensional" means herein that the thickness is much less than the remaining two dimensions.

In an embodiment, there is placed in the oscillatable element at least one cavity and/or at least one passageway in such a manner that two symmetric legs form, by means of which the oscillatable element is secured on the membrane. The cavity or passageway reduces the stiffness of the oscillatable element. The legs are connected with the membrane in the two securement regions. Preferably, the legs are positioned at a location of maximum deflection of the membrane.

In an embodiment, the process variable is a rheological property, especially the viscosity, and/or the density and/or a limit-level of the medium in a container.

BRIEF DESCRIPTION OF THE DRAWINGS

The invention will now be explained in greater detail based on the appended drawing, the figures of which show, in each case schematically, as follows.

DETAILED DISCUSSION IN CONJUNCTION WITH THE DRAWINGS

Figure 1:
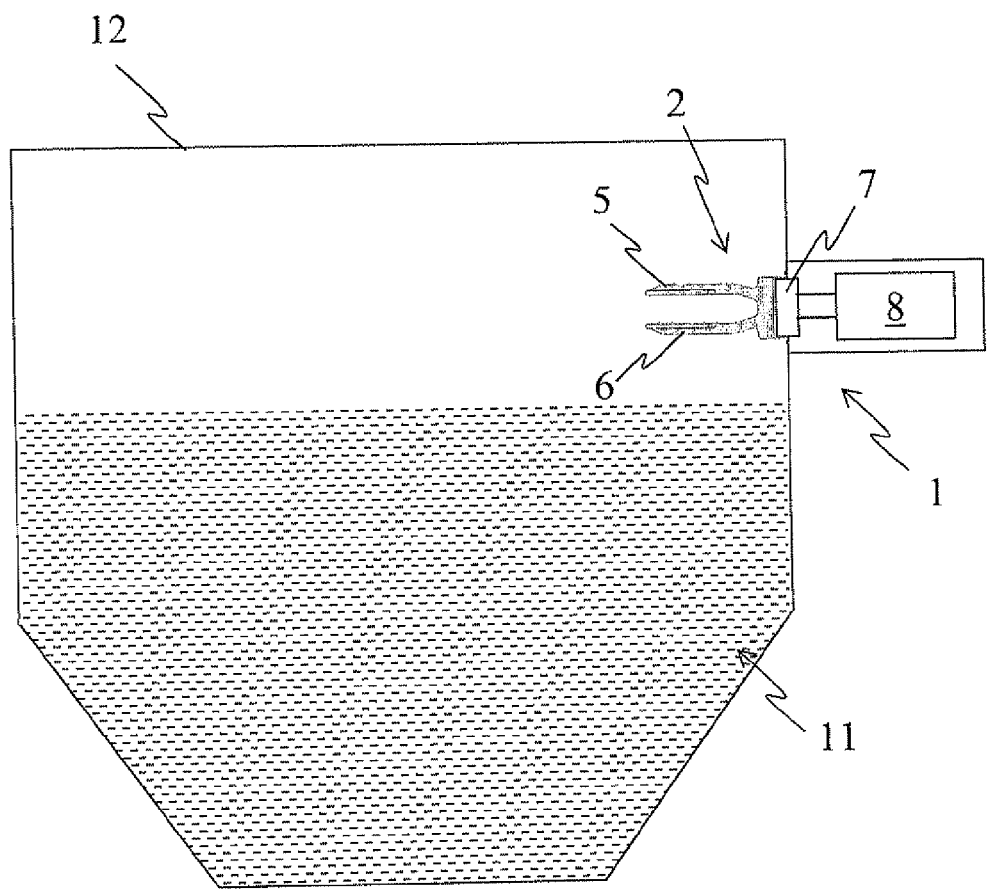
FIG. 1 is a container and a vibronic measuring device.

FIG. 1 shows a container 12 partially filled with a liquid 11. Mounted in the wall of the container 12 at a certain height in the container 12 is a vibronic measuring device 1. The measuring device 1 protrudes with an oscillatable unit 2 in the form of two paddles 5, 6 formed on a membrane 3 into the interior of the container 12. The membrane 3 terminally closes a tubular housing of the measuring device 1. Located in the housing and in contact with the rear face of the membrane 3 facing away from the interior of the container 12 is a driving/receiving unit 7. This deforms the membrane 3 periodically in such a manner that the paddles 5, 6 oscillate. Preferably, the driving/receiving unit 7 is embodied as a piezoelectric bimorph or stack drive. A piezoelectric drive element can also serve as a receiver by tapping a feedback voltage across a resistor. Alternatively, one or more separate driving elements and receiving elements are present.

Connected with the driving/receiving unit 7 is a control/evaluation unit 8, which is an electronics unit, preferably one having at least one microcontroller. Control/evaluation unit 8 controls the oscillation excitement by means of the driving/receiving unit 7 and receives from this the electrical received signal dependent on the oscillations of the oscillatable unit for evaluation with reference to the process variable to be determined or monitored. In the case of an electromechanical conversion unit in the form a driving/receiving unit 7 having one or more piezoelectric elements, the control/evaluation unit 8 supplies the driving/receiving unit 7 with an electrical exciter signal in the form of an alternating voltage. The frequency of the alternating voltage is preferably predeterminable via an oscillatory circuit in such a manner that between exciter signal and received signal a predeterminable phase shift is present. The control of the frequency can occur, in such case, analogy and/or digitally.

Compared to a conventional vibronic measuring device for fill level-, density- and/or viscosity measurement, the measuring device 1 of the invention differs structurally at least in the embodiment of the driving/receiving unit 7. Because of the particular arrangement of the drive element 77, respectively the drive elements 71, 72, a torsion mode is excitable instead of bending modes. Also in the case of a torsional oscillation, the said process variables are determinable based on the oscillation characteristics. Evaluatable oscillation characteristics include especially the frequency, the amplitude and/or the phase shift between exciter- and received signal. An advantage of exciting to torsional oscillations is that damping effects arising from medium 11 moved with the oscillatable elements 5, 6 are significantly lessened and, thus, high viscosity media 11 do not degrade or impede the measuring. Additionally, with the measuring device 1 of the invention, viscosity is reliably determinable.

In a form of embodiment, control/evaluation unit 8 produces an exciter signal having a predetermined frequency, which is suitable for exciting the oscillatable elements 5, 6 to execute torsional oscillations. This frequency can be determined, for example, by simulation and is, consequently, definitely predeterminable, so that the measuring device 1 is immediately ready for use after installation. Preferably, the frequency is selected in such a manner that the oscillatable elements 5, 6 oscillate at resonance. In this way, a maximum effect is achieved. In an advantageous embodiment, the oscillatable unit 2 is, respectively especially the oscillatable elements 5, 6 are, dimensioned in such a manner that the lowest mode excitable by the driving/receiving unit 7 is the desired pure torsion mode. Control/evaluation unit 8 can, in this case, for the finding the suitable frequency, move with rising frequency through a frequency range in the working range of the oscillatable unit 2, in order therewith, automatically, to excite the torsion mode.

Figure 2:
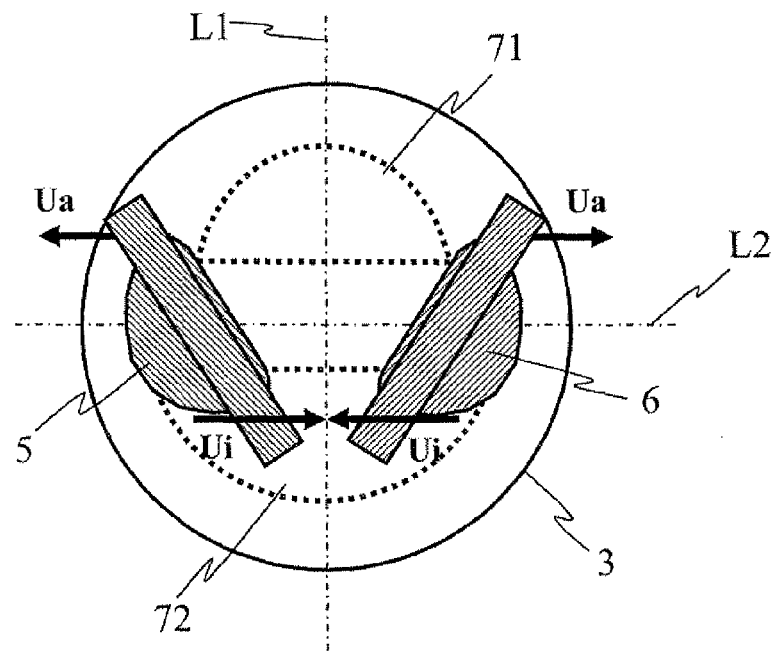
FIG. 2 is a plan view of an oscillatable unit coupled with driving/receiving unit.

FIG. 2 shows a schematic view of the details of significance for the membrane 3 with two oscillatable elements 5, 6 and two drive elements 71, 72 during torsional movement. The deflections of the oscillatable elements 5, 6 and the deformations of the drive elements 71, 72 are, in such case, shown greatly enlarged. The two oscillatable elements 5, 6 are arranged symmetrically relative to a central axis L1 and on an outer surface of the membrane 3 facing the medium 11. In this example of an embodiment, the oscillatable elements 5, 6 and the membrane 3 share a monolithic 2-dimensional contact surface, i.e. the first securement region 91 and the second securement region 92 of the oscillatable element 5, 6 merge with one another.

For example, the oscillatable elements 5, 6 and the membrane 3 are manufactured of a metal, especially stainless steel, and are welded with one another. The oscillatable elements 5, 6 are embodied with paddle shape and have a connection region for securement to the membrane 3 and a 2-dimensional element 61. Alternatively, the oscillatable elements 5, 6 can also be rod shaped, especially cylindrical. In the case of a cylindrical oscillatable element 5, 6, the added-mass effect is especially small in the torsion mode.

Located on the rear face of the membrane 3, i.e. on that face, on which no oscillatable elements 5, 6 are arranged and which faces an interior of the measuring device 1, are two piezoelectric drive elements 71, 72. These are shaped as circular sections and are oriented symmetrically relative to a central axis L2 of the membrane 3. The two central axes L1 and L2 extend orthogonally to one another.

The two drive elements 71, 72 have the same direction of polarization. Such extends in the axial direction, i.e. perpendicular to the plane of the membrane. The exciter signals, which the control/evaluation unit 8 supplies to the two sending electrodes 73, 74 applied on the drive elements 71, 72, are alternating voltage signals, which have the same frequency but a phase shift of 180° relative to one another. In this way, the two drive elements 71, 72 execute thickness oscillations of opposite phase.

In this figure, the first drive element 71 thickens and accordingly its surface expanse shrinks. The corresponding membrane section warps outwardly, so that, on the two securement regions of the oscillatable elements 5, 6 located in this section, a force Ua acts away from the central axis L1. The drive element 72, in contrast, expands, so that the corresponding section of the membrane 3 warps inwardly and the two securement regions of the two oscillatable elements 5, 6 located in this section experience a force Ui directed in toward the central axis L1. Since the oscillatable elements 5, 6 are each secured half on the one section and half on the other section of the membrane 3, the two securement regions of an oscillatable element 5, 6 move in opposite directions. In this way, there arise in the two securement regions opposed torques and this leads to torsion of the oscillatable elements 5, 6.

This type of excitation of the oscillatable elements 5, 6 for torsional oscillations is especially simply implementable.

In the case of exciting the two sections of the membrane 3 to opposite phase oscillations, there exists, due to the symmetry of the two oscillatable elements 5, 6, for each arising force a corresponding counterforce, so that the oscillatory system is decoupled. An embodiment with only one oscillatable element 4 is, however, likewise possible. In this case, however, the securement of the membrane 3 should be sufficiently solid that forces acting on it do not influence the measurement.

The viscosity is proportional to an angular deflection of the oscillatable element 5, 6 in the viscous medium 11 relative to a corresponding angular deflection in air or vacuum. Control/evaluation unit 8 determines the viscosity of the medium 11, for example, based on the amplitude of the received signal. This is tappable, for example, as a voltage drop across a resistor in the circuit of the sending electrodes 73, 74. For monitoring a predetermined limit level of the medium 11, respectively for detecting whether the medium 11 ex- or sub-ceeds the predetermined limit-level, the control/evaluation unit 8 evaluates a frequency change of the torsional oscillations.

Figures 3A, 3B:
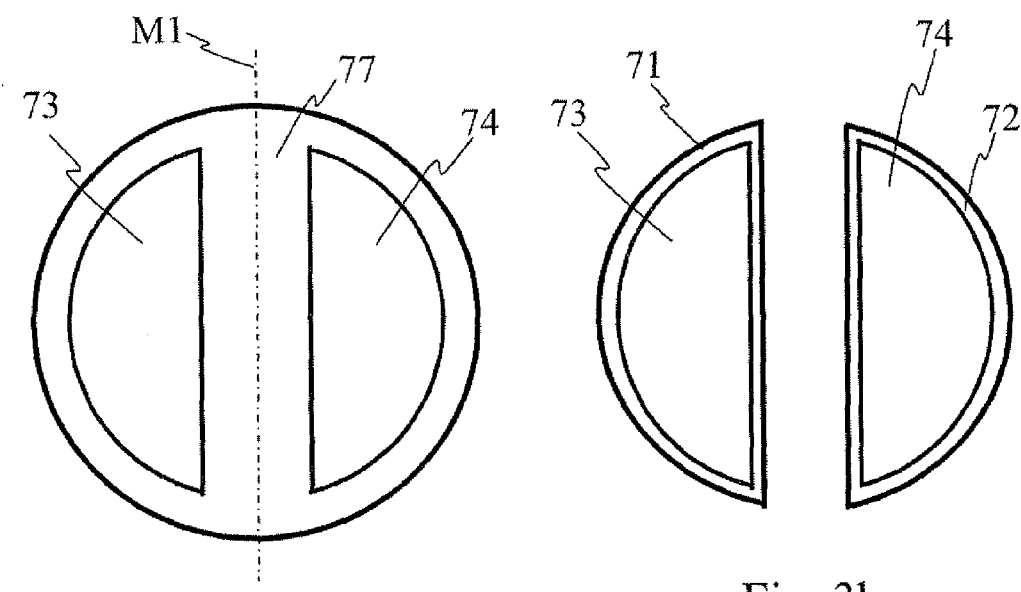
FIG. 3a is an embodiment of a one-part drive element.
FIG. 3b is an embodiment of a two-part drive element.

FIGS. 3a and 3b show two variants of suitable drives. FIG. 3a shows a disc shaped piezoelectric drive element 77, to which are applied two sending electrodes 73, 74. The polarization direction of the piezoelectric drive element 77 extends perpendicularly to the plane of the membrane. Sending electrodes 73, 74 each have the shape of a circular section and are embodied symmetrically to a middle axis M1 of the drive element 77. The two sending electrodes 73, 74 form two regions electrically separated from one another. The drive element 77 is applied in the case of an apparatus of the invention in such a manner on the rear face of the membrane 3 facing away from the medium that the middle axis M1 of the drive element 77 and the central axis L1 of the membrane 3, which forms the symmetry axis for the two oscillatable elements 5, 6, extend orthogonally to one another.

FIG. 3b shows an embodiment with two identically embodied drive elements 71, 72. The first drive element 71 and the second drive element 72 are shaped as circular sections. On one of their two flat faces, in each case, a sending electrode 73, 74 is applied. The mounting on the membrane 3 occurs in such a manner that the two drive elements 71, 72 are arranged symmetrically to the longitudinal axis L2 and the sending electrodes 73, 74 are located on those drive element faces, which face away from the membrane 3. Because of supplying the second sending electrode 74 with an exciter signal, which is shifted phase by 180° relative to the exciter signal supplied to the first sending electrode 73, the two drive elements 71, 72, respectively the two regions of the drive element 7, are excitable to thickness oscillations of opposite phase.

In a variant, the two drive elements 71, 72 or the two regions of the drive element 77 are polarized in opposite directions. The sending electrodes 73, 74 are, in this case, supplied with the same exciter signal.

The exciting of a peripherally secured membrane by means of a piezoelectric element to opposite phase oscillations, respectively to oscillations in the first harmonic wave, is described in Offenlegungsschrift DE 10 2007 057 124 A1, so that such excitation is not explored in greater detail here. Information given there is analogously applicable here and holds also for the two part embodiment according to FIG. 3b.

Figure 4:
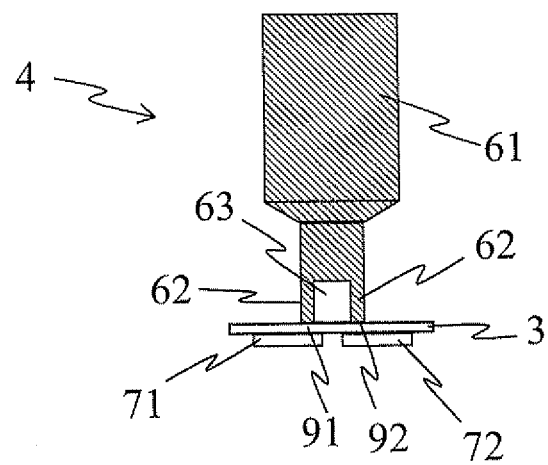
FIG. 4 a form of embodiment of an oscillatable element.

FIG. 4 illustrates a form of embodiment of an oscillatable element 4, which can be provided as a single oscillatable element 4 on the membrane 3, or which forms one of two oscillatable elements 5, 6 symmetrically secured on the membrane 3. Oscillatable element 4 possesses the shape of a paddle, which is composed of a 2-dimensional element 61 and a tapered connection region. The connection region is located near the membrane 3 and is secured to such. Provided in the connection region is a passageway 63. The provision of passageway 63 leads to the formation of two legs 62, which are connected with the membrane 3 at respective securement regions 91, 92.

Beneath the first securement region 91, on the oppositely lying face of the membrane 3, a first drive element 71 is arranged, while below the second securement region 92 a second drive element 72 is arranged. Upon supplying the two drive elements 71, 72 with suitable exciter signals such as already described, the two sections of the membrane 3, in which the two securement regions 91, 92 are located, move in opposite directions. Acting on the two legs 62 are torques in opposed directions. This leads such as in the case of an oscillatable element 4 without passageway 63 to a torsional movement of the oscillatable element 4. However, the passageway 63, on the one hand, reduces the stiffness of the connection region and, on the other hand, makes the membrane 3 freer in its movement. In this way, a torsional movement of larger amplitude is enabled.

The invention claimed is:

1. An apparatus for determining and/or monitoring at least one process variable of a medium, comprising:
an oscillatable unit, which has a membrane and at least one oscillatable element, said oscillatable element is secured to said membrane at least in a first securement region and in a second securement region;
at least one driving/receiving unit, which excites said oscillatable unit to execute mechanical oscillations and produce a received signal dependent on the oscillations of said oscillatable unit; and
a control/evaluation unit, which evaluates the received signal with reference to the process variable, wherein:
said driving/receiving unit is embodied in such a manner and arranged on a rear face of said membrane facing away from said oscillatable element that said driving/receiving unit excites said membrane to execute oscillations in such a manner that a first section of said membrane, in which said first securement region is located, and a second section of said membrane, in which said second securement region is located, execute oscillations of opposite phase, and said oscillatable element executes torsional oscillations.

2. The apparatus as claimed in claim 1, wherein:
said oscillatable element is at least sectionally paddle shaped or rod shaped.

3. The apparatus as claimed in claim 1, wherein:
said driving/receiving unit includes at least one piezoelectric drive element.

4. The apparatus as claimed in claim 3, wherein:
said piezoelectric drive element is polarized perpendicularly to a plane, in which said membrane lies in a relaxed state.

5. The apparatus as claimed in claim 1, wherein:
said driving/receiving unit has at least two regions electrically insulated from one another and is arranged in such a manner that the first region extends over said first section of said membrane, in which at least said first securement region of said oscillatable element is located and that the second region extends over said second section of said membrane, in which at least said second securement region of said oscillatable element is located.

6. The apparatus as claimed in claim 1, wherein:
a first oscillatable element and a second oscillatable element are secured on said membrane essentially symmetrically to a central axis of said membrane.

7. The apparatus as claimed in claim 5, wherein:
said driving/receiving unit and said two oscillatable elements are arranged in such a manner relative to one another that the first region of said driving/receiving unit extends over the first section of said membrane, in which at least said first securement region of said first oscillatable element and said first securement region of said second oscillatable element are located, and
that the second region of said driving/receiving unit extends over the second section of said membrane, in which at least said second securement region of said first oscillatable element and said second securement region of said second oscillatable element are located.

8. The apparatus as claimed in claim 4, wherein:
the two regions of said driving/receiving unit have, in each case, a sending electrode and said control/evaluation unit supplies said sending electrodes, in each case, with an alternating voltage signal of equal frequency;
for the case, in which the two regions have the same polarization direction, the two alternating voltage signals have relative to one another a phase shift of 180° and for the case, in which the two regions have opposite directions of polarization, the two alternating voltage signals are of equal phase.

9. The apparatus as claimed in claim 1, wherein:
there is placed in sai oscillatable element at least one cavity and/or at least one passageway in such a manner that two symmetric legs form, by means of which said oscillatable element is secured on said membrane.

10. The apparatus as claimed in claim 1, wherein:
the process variable is a rheological property of the medium in a container.

11. The apparatus as claimed in claim 10, wherein:
the process variable is one of: viscosity and/or density, and/or a limit-level of the medium in a container.

* * * * *